United States Patent [19]

Kanno et al.

[11] Patent Number: 4,598,733
[45] Date of Patent: Jul. 8, 1986

[54] APPARATUS FOR DETECTING THE VOLUME OF BLOOD IN A BLOOD RESERVOIR

[75] Inventors: Michio Kanno, Saitama; Atsuhiko Nogawa, Ninomiya, both of Japan

[73] Assignee: Terumo Corporation, Tokyo, Japan

[21] Appl. No.: 736,440

[22] Filed: May 21, 1985

[30] Foreign Application Priority Data

May 23, 1984 [JP] Japan .................. 59-104191

[51] Int. Cl.⁴ .................. F16K 31/126; A61M 1/03
[52] U.S. Cl. .................. 137/406; 73/299;
128/DIG. 3; 128/DIG. 13; 340/611; 340/614;
340/626; 422/45; 604/65; 604/67; 604/118;
604/245
[58] Field of Search .................. 73/299; 128/DIG. 3,
128/DIG. 13; 137/386, 403, 406; 340/611, 614,
626; 422/44, 45; 604/4, 65, 67, 118, 245

[56] References Cited

U.S. PATENT DOCUMENTS

| | | | |
|---|---|---|---|
| 3,601,124 | 8/1971 | Petree | 604/65 |
| 3,641,543 | 2/1972 | Rigby | 128/DIG. 13 |
| 3,890,969 | 6/1975 | Fischel | 604/67 |
| 4,121,584 | 10/1978 | Turner et al. | 128/DIG. 13 |
| 4,261,388 | 4/1981 | Shelton | 604/65 |
| 4,385,630 | 5/1983 | Gilcher et al. | 604/67 |
| 4,394,862 | 7/1983 | Shim | 604/67 |
| 4,469,480 | 9/1984 | Figler et al. | 604/245 |

Primary Examiner—G. L. Walton
Attorney, Agent, or Firm—Frishauf, Holtz, Goodman & Woodward

[57] ABSTRACT

In combination with a blood reservoir, a blood volume detecting apparatus is used to ensure safe operation of the reservoir which includes a conduit in fluid communication with a lower part of said blood reservoir, a diaphragm associated with the other end of the conduit and movable by a differential hydraulic pressure applied by the blood through the conduit, and means for detecting the swelling and contracting movement of the diaphragm.

12 Claims, 12 Drawing Figures

APPARATUS FOR DETECTING THE VOLUME OF BLOOD IN A BLOOD RESERVOIR

BACKGROUND OF THE INVENTION

This invention relates to an apparatus for detecting the volume of blood in a blood reservoir.

An oxygenator circuit for an extracorporeal circulation is often employed for temporarily substituting the function of the heart during an open-heart surgery. A blood reservoir for regulating blood flow is incorporated in such an oxygenator circuit. However, the oxygenator circuit involves dangerous problems such as breakage of an entrance tube to the reservoir and a decrease in blood volume due to increased hemorrhage or urine.

Two types of blood reservoirs have been traditionally used, that is, an open-type reservoir having an upper end open to the atmosphere and a closed-type reservoir in the form of a soft bag. In the open-type blood reservoir, when the blood volume is decreased to zero, air can be sucked into the blood outlet line tube and sent to the patient, which leads to an extremely dangerous situation. In the closed-type blood reservoir, when the blood volume is decreased to zero, air is not sucked as opposed to the open-type blood reservoir, but instead, a negative pressure can be exerted.

There is the need for an apparatus for detecting the volume of blood in a blood reservoir.

In conventional open-type blood reservoirs, various types of detectors for monitoring the fluid level have been employed as blood volume detecting apparatus. Closed-type blood reservoirs, however, are unamenable to such automatic detection as done in the open-type blood reservoirs because no fluid level is formed in the closed-type reservoirs. A side tube may also be affixed to the closed-type blood reservoir in order to provide a visible fluid level. However, air can be sucked through the side tube to impair the advantage of the closed-type blood reservoir.

The blood volume in the closed-type blood reservoir may also be detected by measuring the total weight of the blood reservoir. However, several tubes connected to the blood reservoir render the measurement inaccurate.

The volume of blood in the bag-shaped reservoir may be judged by observinig the contraction of the bag reservoir. In this case, a large-sized detector is required and the measurement becomes inaccurate as the bag is irregularly deformed. The level to be detected is uncontrollable in some cases.

SUMMARY OF THE INVENTION

It is, therefore, an object of the present invention to provide an apparatus for detecting the volume of blood in a blood reservoir which is capable of accurately detecting the blood volume without losing the advantage of a closed-type blood reservoir, capable of changing the blood level to be detected, and also applicable to an open-type blood reservoir.

According to the present invention, there is provided an apparatus for detecting the volume of blood in a blood reservoir comprising
a conduit having one end in fluid communication with a lower part of the blood reservoir,
a membrane associated with the other end of the conduit and movable by a differential hydraulic pressure applied by the blood through the conduit, and
means for detecting the movement of the membrane.

Several preferred embodiments are described below.

(i) The detecting means includes a detector for detecting the movement of the membrane to produce an output and an alarm which is actuated in response to the output of the detector.

(ii) The detecting means includes a detector for detecting the movement of the membrane to produce an output and control means which is actuated in response to the output of the detector to control the flow of blood into and out of the blood reservoir.

(iii) The membrane is presented by a bag connected to the conduit.

(iv) The membrane is combined with a rigid casing affixed to the conduit.

(v) The detecting means includes a pair of light emitting and sensing elements.

DETAILED DESCRIPTION OF THE INVENTION

Figure 1:
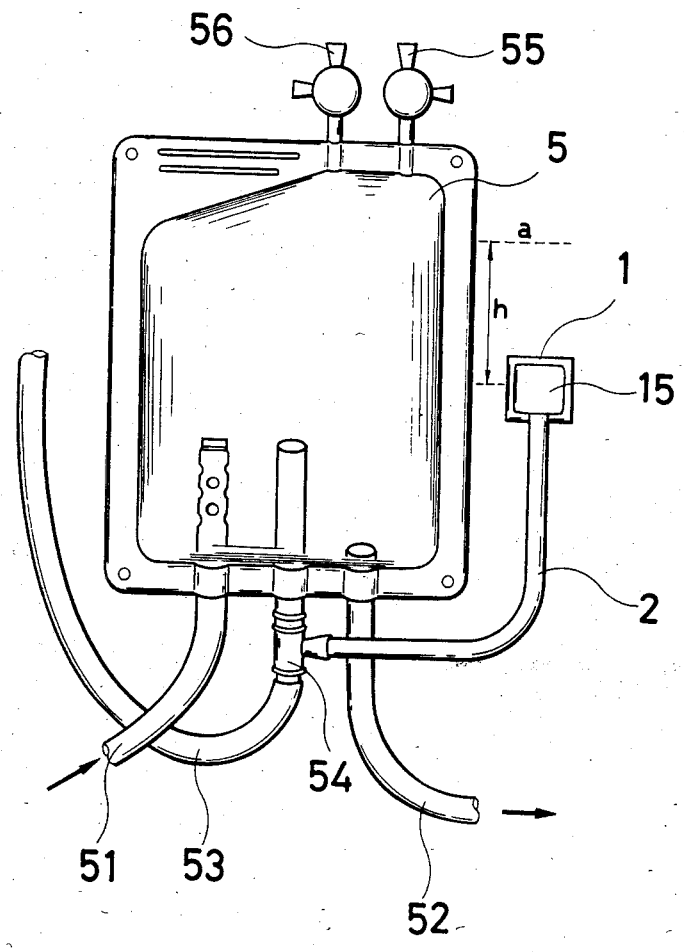
FIG. 1 is an elevation of one preferred embodiment of the blood volume detecting apparatus of the present invention.

Referring to FIG. 1, there is illustrated an apparatus for detecting the volume of blood in a blood reservoir according to one preferred embodiment of the present invention.

A blood reservoir 5 is shown in the form of a closed bag made of a soft material such as flexible resins.

A blood incoming line tube 51, a blood outgoing line tube 52, and a cardiotomy line tube 53 are connected to a lower portion, preferably the bottom of the blood reservoir 5 in fluid communication. Air-vent ports 55 and 56 are provided in an upper portion, preferably the top of the blood reservoir 5.

The cardiotomy line tube 53 serves as a blood outgoing conduit in communication with the lower portion of the closed blood reservoir 5 and is provided with a branch connector 54. The branch connector 54 has a branch which removably is connected to one end of a conduit 2 constituting the blood volume detecting apparatus of the present invention. The conduit 2 is usually a tube of flexible resin.

A bag 1 for detection is connected to the other end of the conduit 2. The bag 1 takes the form of a bag made of flexible material such as plasticized polyvinyl chloride, polyurethane, silicone rubber and polyethylene. The surface of the bag is thus movable by a differential hydraulic pressure applied by the blood through the conduit 2. In one preferred embodiment according to the present invention, the surface of the bag 1 connected to the conduit 2 constitutes a detecting membrane or diaphragm 15.

For the purpose of detecting precision, preferably the conduit 2 has a length of about 15 to 50 cm and an inside diameter of about 1.5 to 5 mm, and the bag 1 has an effective area of about 0.2 to 20 cm and a maximum volume of about 0.5 to 5 ml.

Next, the motion of the membrane 15 is described. The wall of blood reservoir 5 made of soft material allows the atmospheric pressure to be transmitted therethrough to the blood in the reservoir.

When the blood reservoir 5 contains fluid or blood, a pressure corresponding to the potential equivalent fluid level designated by line a in FIG. 1 is conducted to the bag 1 through the cardiotomy line tube 53, branch connector 54 and conduit 2. The differential hydraulic pressure or head, indicated by h in FIG. 1, between the potential equivalent fluid level and the bag level is thus applied to the bag 1. In this embodiment, the potential equivalent fluid level is given by the fluid level at an open end in communication with the reservoir 5, usually in a cardiotomy reservoir (not shown). The bag 1 of soft material is swollen by an internal pressure when the head h is positive, whereas it is flattened out when the head h is zero or negative. Since the head h is a relative position, the blood level to be detected can be changed by regulating the position or height of the bag 1.

Various types of conventional detectors may be employed as a detector of means for detecting the movement of the bag 1 or membrane 15.

Figure 2:
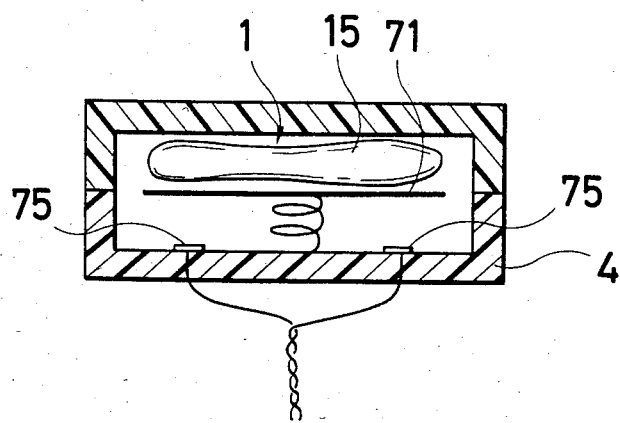
FIG. 2 is a cross-sectional view of one example of the membrane and the detector.

One example of the detector is illustrated in FIG. 2. The bag 1 is housed in a casing 4. The movement of the bag 1 is detected by means of a metal plate 71 which is moved by swelling of the bag 1 into contact with terminals 75. This detector, however, has a problem of malfunction due to poor water resistance as it is often exposed to blood and physiological saline on use.

It is, therefore, desirable to employ a detector which optically detects the movement of a membrane or diaphragm.

Figure 3:
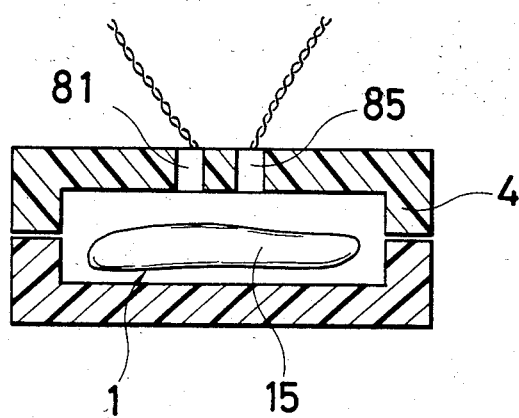
FIG. 3 is a cross-sectional view of another example of the membrane and the detector.

FIG. 3 illustrates another example of the detector. The bag 1 is housed in casing 4, in which a pair of light emitting and sensing elements 81 and 85 are placed.

Figure 4A:
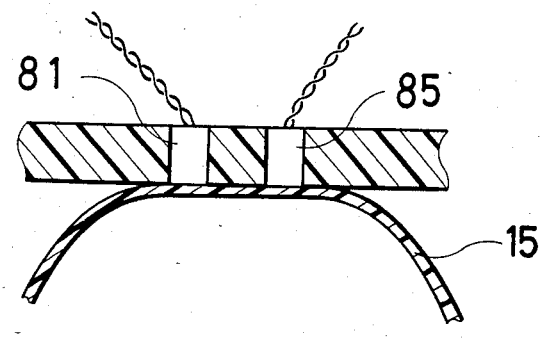
FIGS. 4a and 4b are enlarged cross-sectional views of the membrane and detector in FIG. 3, illustrating the swollen and flattened membranes in relation to the detector.
Figure 4B:
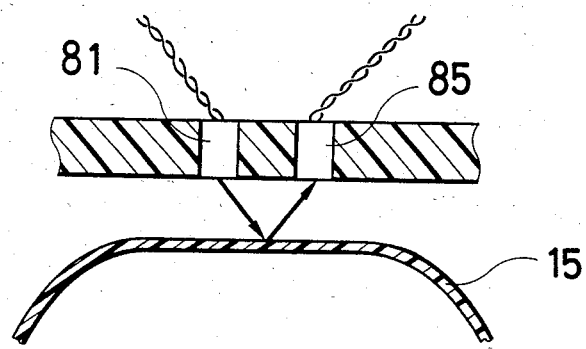

When the bag 1 is swollen, the bag upper surface that constitutes the membrane 15 is in close contact with the inner wall of the casing 4 as shown in FIG. 4a. Then the light sensing element 85 does not react. When the bag 1 is flattened out, the bag upper surface or membrane 15 is spaced apart from the casing inner wall as shown in FIG. 4b. Then light from the light emitting element 81 is reflected by the bag upper surface toward the sensing element 85 which produces a predetermined detection signal.

In such optical detection using reflected light from the membrane 15, no mechanically movable part is involved in the detector which provides for more reliable detection.

The detector may be prepared by molding a potting resin into a one-piece casing having photoelectric elements built therein, which exhibits improved water resistance. With this process, the detector itself is advantageously size reduced so that it may be readily and movably mounted to a holder on the blood reservoir with a clamp and the like.

The detector may most preferably be constructed such that the membrane 15a in swollen state covers the light emitting element 81 and/or light sensing element 85, usually both, to shield light emission; the amount of reflected light reaches maximum when the membrane 15 is spaced apart from the light emitting and sensing elements 81 and 85 a distance of about 0.1 to 0.8 mm after the commencement of shrinkage of the bag; and the reflected light does not reach the light sensing element 85 when the bag 1 is completely flattened out. With this construction, even the slightest movement of the membrane 15 in relation to the light emitting element 81 and/or light sensing element 85 can be detected, providing for remarkably improved reactivity and precision of detection.

Figure 4C:
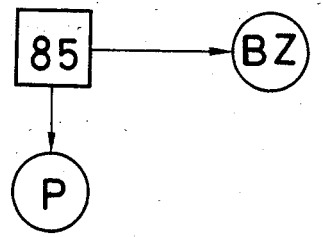
FIG. 4c is a block diagram illustrating a network of the detector with alarm and control means.

As shown in FIG. 4c, an alarm such as a buzzer BZ or control means for controlling the flow of blood into and out of the blood reservoir as by stopping a blood pump P associated therewith may be provided so that they are actuated in response to an output of the detector or a signal from the light sensing element 85.

Since the bag 1 is made of soft material as stated above, the bag surface itself functions as the detecting membrane or diaphragm 15 and the bag 1 may be manually squeezed. Prior to an operation, air remaining in the bag can be squeezed out and vented through the port 55 at the top of the blood reservoir 5. The residual air may also be removed by means of a syringe from the conduit 2.

Figure 5:
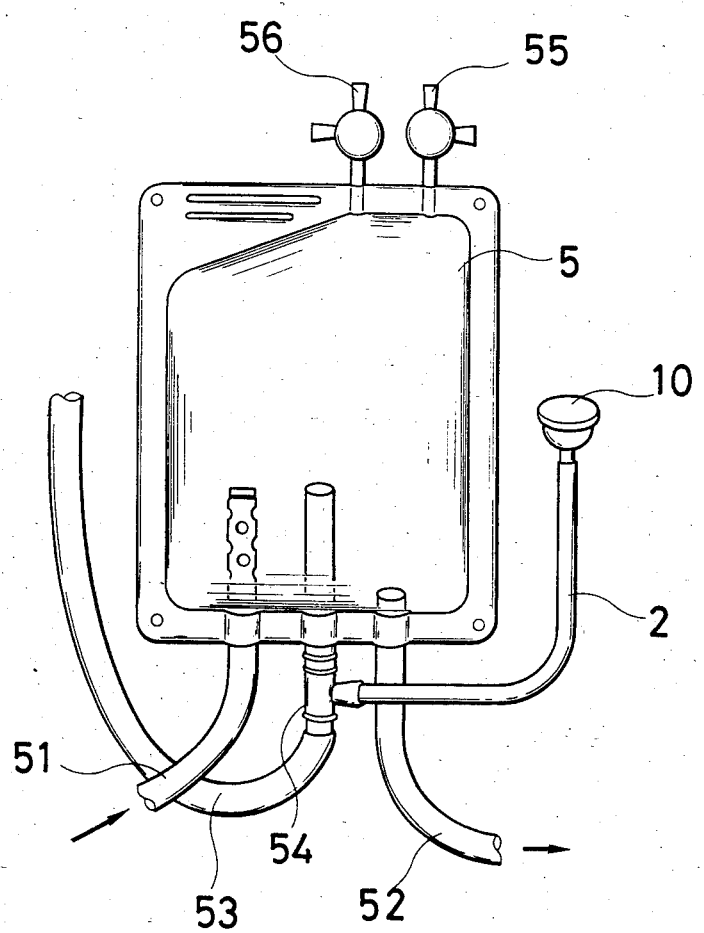
FIG. 5 is an elevation of another preferred embodiment of the blood volume detecting apparatus of the present invention.
Figure 6:
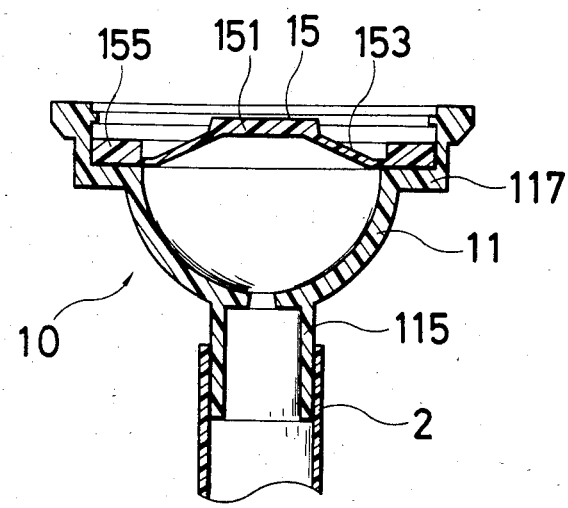
FIG. 6 is an enlarged cross-sectional view of the diaphragm assembly used in FIG. 5.
Figure 7:
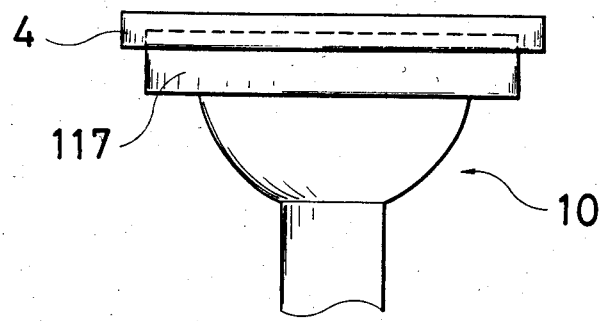
FIG. 7 is an elevation of the detector having the diaphragm assembly of FIG. 6.

Referring to FIGS. 5, 6 and 7, there is illustrated a more preferred embodiment of the blood volume detecting apparatus of the present invention.

For more accurate detection and simple air venting operation, detecting means shown in FIGS. 5, 6 and 7 as comprising a membrane or diaphragm 15 combined with a casing 11 to form a diaphragm assembly 10 is preferable rather than the detector bag 1.

The casing 11 is a cup-shaped rigid body having a curved concave inner surface, preferably a spherical inner surface and connectable to the conduit 2. The casing 11 is provided at a suitable location, typically at the apex, of its curved surface with a port member 115 which is connected to the conduit 2 to provide fluid communication between the casing interior and the conduit 2.

The casing 11 is provided at the base of its curved surface with a flange 117 to which the diaphragm 15 is secured at the periphery. Various bonding methods such as adhesive bonding, heat sealing, and mechanical press bonding may be employed to secure the diaphragm 15 to the casing 11.

This diaphragm assembly 10 can be easily vented simply by pressing the diaphragm 15 to the curved inner surface of the casing 11 with a finger.

Since the diaphragm 15 is necessarily attracted to the casing 11 under a negative pressure, the possible malfunction of detecting means, particularly in the form of an optical sensor is minimized, resulting in improved reliability.

Further, as the casing comprises a rigid body, the detector may conveniently be mounted or supported.

The diaphragm 15 for detection may preferably include a thick-walled central portion 151, a thin-walled annular portion 153 concentrically surrounding the central portion 151, and a thick-walled annular flange 155 concentrically surrounding the annular portion 153 as shown in FIG. 6. The annular portion 153 connects the central portion 151 to the flange 155 such that the central portion 151 protrudes outward and the annular portion 153 slants accordingly. Then the diaphragm 15 is movable over an increased distance and provides for easy and complete venting with a finger. This configuration allows the diaphragm to move or respond to a pressure change in a stable and delicate manner, leading to increased reliability.

Non-toxic, relatively rigid resin materials such as polycarbonate, polypropyrene, polyethylene, polyvinyl chloride, polyester, acrylic resin, polystyrene and the like may preferably be used to form the casing 11 of the diaphragm assembly 10.

The diaphragm 15 may preferably be formed from elastomers such as plasticized polyvinyl chloride, polyurethane, silicone rubber, polyethylene and the like to a thickness between 0.03 and 3 mm.

Preferably, the diaphragm 15 has an effective area of about 0.2 to 20 cm$^2$, the diaphragm assembly 10 has a maximum volume of about 0.2 to 20 cm$^3$, and the conduit 2 has a length of about 15 to 50 cm and an inside diameter of about 1.5 to 5 mm.

The movement of the diaphragm 15 of the assembly 10 may preferably be detected by optical means, for example, using reflection of light.

The diaphragm assembly may preferably be constituted such that the light emitting element 81 and/or the light sensing element 85 are shielded by the swollen diaphragm 15 and the amount of reflected light becomes maximum when the diaphragm 15 is slightly flattened.

As shown in FIG. 4c, a buzzer BZ or control means for controlling the flow of blood from the blood reservoir may preferably be actuated in response to a signal from the light sensinig element 85.

Therefore, the detecting means comprises a diaphragm assembly, a detector consisting of a pair of light emitting and sensing elements, and an alarm such as a buzzer and/or control means for controlling the flow of blood into and out of the blood reservoir.

FIG. 7 illustrates an example of such detecting means wherein the diaphragm assembly 10 is fitted in a cover 4 having a battery, light emitting and sensing elements, a buzzer, and other optional elements built therein although these elements are not shown.

Figure 8:
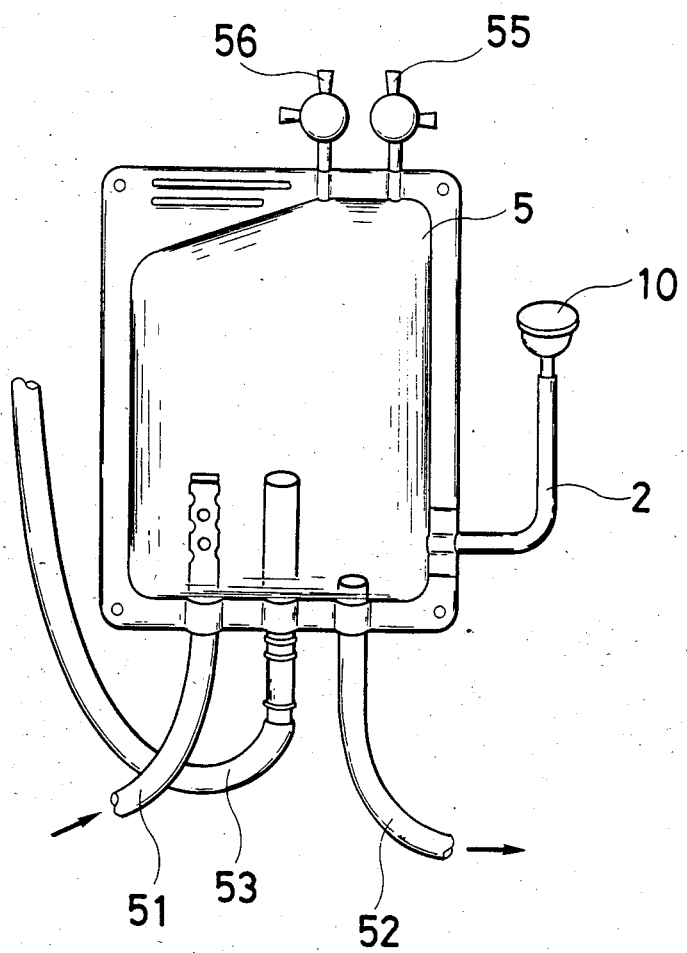
FIGS. 8, 9 and 10 are elevations illustrating different embodiments of the apparatus of the present invention, respectively.
Figure 9:
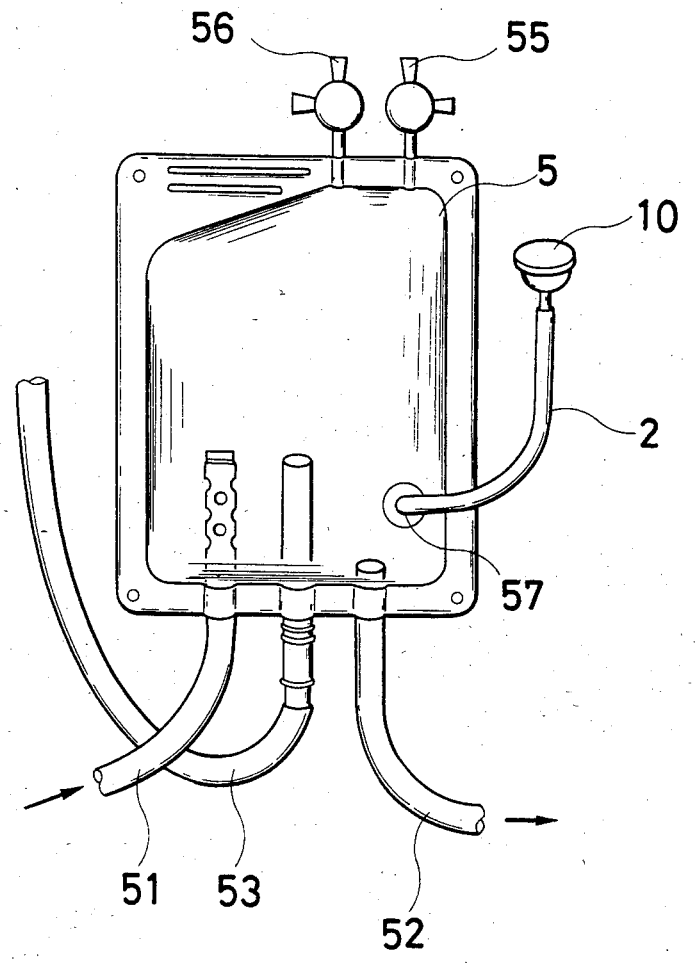

Although the conduit 2 in fluid communication with the detector bag 1 or the diaphragm assembly 10 is connected to the branch connector 54 in the cardiotomy line tube 53 in the embodiment shown in FIG. 1 or 5, it may be directly connected to the bag-shaped blood reservoir by fusing during manufacture as shown in FIG. 8. The conduit 2 may also be connected to an attachment port 57 in a lower portion of the blood reservoir 5 as shown in FIG. 9.

Figure 10:
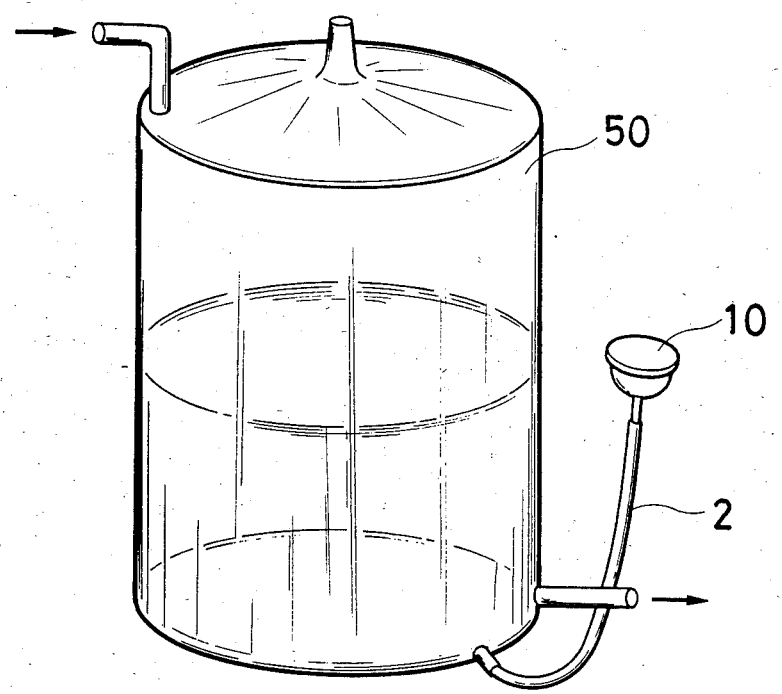

The blood volume detecting apparatus according to the present invention may be used in combination with an open rigid blood reservoir 50 as shown in FIG. 10, as well as the closed soft blood reservoir as fully described above.

The blood volume detecting apparatus of the present invention has many advantages over conventional apparatus as given below.

The use of a membrane or diaphragm which is actuated in response to the potential equivalent fluid level in the blood reservoir allows the blood volume to be detected without detracting from the advantage of the closed blood reservoir that no substantial volume of air is sucked even under a negative pressure.

The detection level can be regulated by changing the vertical position or height of the detector relative to the blood reservoir.

Blood volume detection can be carried out without a substantial modification of the blood reservoir body.

The blood volume detecting apparatus of the present invention is applicable to blood reservoirs of both closed and open types. Particularly when it is combined with a blood reservoir of closed type, the blood volume in the reservoir is detected without sacrificing the advantage of the closed type reservoir.

The provision of an alarm or control means is practically quite advantageous because an alarm signal is automatically produced or the flow of blood into and out of the blood reservoir is automatically controlled.

Precision detection and air-venting operation are ensured when the membrane or diaphragm is comprised of a bag connected to the conduit, and further improved particularly when the diaphragm is combined with a cup casing affixed to the conduit.

Further, the precision detection and water proofness of the detector are improved when light emitting and sensing elements are employed to detect the movement of the diaphragm.

We claim:

1. An apparatus for detecting the volume of blood in a closed-type blood reservoir, comprising:
   a conduct having one end in fluid communication with a lower part of said blood reservoir;
   a membrane associated with the other end of the conduit, said membrane being set at a selected given height relative to said blood reservoir, and said membrane being deformable by a differential hydraulic pressure directly applied by the blood in said blood reservoir through the conduit, said differential hydraulic pressure being a function of the height of said membrane relative to said blood reservoir;
   said conduit being filled with blood so that the space between said membrane and said blood reservoir is filled with blood; and
   means for detecting a deformation of said membrane to thereby detect a volume of blood in said blood reservoir.

2. A blood volume detecting apparatus according to claim 1 wherein said detecting means includes:
   a detector for detecting the movement of the membrane to produce an output; and
   an alarm which is actuated in response to the output of the detector.

3. A blood volume detecting apparatus according to claim 2 wherein said detector comprises light emitting and sensing elements.

4. A blood volume detecting apparatus according to claim 1 wherein said detecting means comprises:
   a detector for detecting the movement of the membrane to produce an output; and
   control means which is actuated in response to the output of the detector to control the flow of blood into and out of the blood reservoir.

5. A blood volume detecting apparatus according to claim 4 wherein said detector comprises light emitting and sensing elements.

6. A blood volume detecting apparatus according to claim 1 wherein said membrane is comprised of a bag connected to the conduit.

7. A blood volume detecting apparatus according to claim 1 wherein said membrane is combined with a casing affixed to the conduit.

8. A blood volume detecting apparatus according to claim 7 wherein said casing is a tapered casing having an open end to which the membrane is secured and sealed.

9. A blood volume detecting apparatus according to claim 8, wherein said casing is a cup-shaped casing including:
a curved concave wall,
a port connectable to the conduit to provide fluid communication between the casing interior and the conduit, and
a flange to which the membrane is secured.

10. A blood volume detecting apparatus according to claim 9, wherein said membrane is circular and includes:
a thick-walled central portion,
a thin-walled annular portion surrounding the central portion, and
a thick-walled annular flange surrounding the annular portion.

11. A blood volume detecting apparatus according to claim 1 wherein said conduit is removably connected to the lower part of said blood reservoir.

12. A blood volume detecting apparatus according to claim 1 wherein the vertical position of the membrane relative to the blood reservoir is variable and resettable, whereby the membrane position provides a movable detection level.

* * * * *

UNITED STATES PATENT AND TRADEMARK OFFICE
CERTIFICATE OF CORRECTION

PATENT NO. : 4,598,733
DATED : July 8, 1986
INVENTOR(S) : M. KANNO et al

It is certified that error appears in the above-identified patent and that said Letters Patent is hereby corrected as shown below:

COLUMN 4, line 3, "reseroir" should read --reservoir--;

COLUMN 4, line 6, after "15", delete "a"; after "in", insert --a--;

COLUMN 5, line 38, "sensinig" should read --sensing--;

COLUMN 6, line 13, "sacrifying" should read --sacrificing--.

Signed and Sealed this

Twenty-seventh Day of January, 1987

Attest:

DONALD J. QUIGG

*Attesting Officer*       *Commissioner of Patents and Trademarks*